United States Patent

Collin

[11] Patent Number: 5,964,227
[45] Date of Patent: *Oct. 12, 1999

[54] METHOD AND SYSTEM FOR TREATING DAMAGED HAIR

[75] Inventor: Steven Joseph Collin, Middletown, Conn.

[73] Assignee: Texturizer, Inc., Hartford, Conn.

[*] Notice: This patent is subject to a terminal disclaimer.

[21] Appl. No.: 08/950,707

[22] Filed: Oct. 15, 1997

Related U.S. Application Data

[60] Division of application No. 08/437,453, May 8, 1995, Pat. No. 5,681,553, which is a continuation-in-part of application No. 08/349,786, Dec. 6, 1994, abandoned.

[51] Int. Cl.$^6$ ........................................... A61K 7/06
[52] U.S. Cl. ..................... 132/209; 424/70.1; 424/70.14
[58] Field of Search ............................... 424/70.14, 70.1; 132/200, 202, 209

[56] References Cited

U.S. PATENT DOCUMENTS

| | | | |
|---|---|---|---|
| 3,527,236 | 9/1970 | Anthony et al. | 132/212 |
| 3,579,632 | 5/1971 | Sonnen | 424/70 |
| 3,683,939 | 8/1972 | Johnsen et al. | 132/7 |
| 3,904,748 | 9/1975 | Eckert et al. | 424/70.14 |
| 4,076,800 | 2/1978 | Marsh et al. | 424/70 |
| 4,128,543 | 12/1978 | Johnsen et al. | 260/123 |
| 4,128,631 | 12/1978 | Lundmark et al. | 424/70 |
| 4,186,188 | 1/1980 | Gumprecht | 424/70.14 |
| 4,206,196 | 6/1980 | Davis | 424/16 |
| 4,220,166 | 9/1980 | Newell | 132/7 |
| 4,220,167 | 9/1980 | Newell | 132/7 |
| 4,374,125 | 2/1983 | Newell | 424/70 |
| 4,906,460 | 3/1990 | Kim et al. | 424/70 |
| 4,906,461 | 3/1990 | Chambers | 424/74 |
| 4,913,898 | 4/1990 | Altobelli et al. | 424/70 |
| 4,931,274 | 6/1990 | Barabino et al. | 424/489 |
| 4,970,067 | 11/1990 | Panandiker et al. | 424/70 |
| 5,217,711 | 6/1993 | Oliveira | 514/21 |
| 5,254,336 | 10/1993 | Hoshowski et al. | 424/70.1 |
| 5,466,680 | 11/1995 | Rudy | 514/57 |
| 5,681,553 | 10/1997 | Collin | 424/70.14 |

FOREIGN PATENT DOCUMENTS 9311737   6/1993   WIPO.

*Primary Examiner*—Robert H. Harrison
*Attorney, Agent, or Firm*—Cummings & Lockwood

[57] ABSTRACT

The present invention provides a process of treating damaged hair and a system of formulations for carrying out the process. Treatment according to the invention incorporates protein into the structure of damaged hair by the use of an aqueous solution including an acid and a positively charged electrolyte.

7 Claims, No Drawings

METHOD AND SYSTEM FOR TREATING DAMAGED HAIR

This is a divisional application Ser. No. 08/437,453 filed on May 5, 1995 now U.S. Pat. No. 5,681,553 which is a Continuation in Part of application Ser. No. 08/349,786, filed on Dec. 6. 1994, now abandoned.

BACKGROUND OF THE INVENTION

The present invention relates generally to the treatment of damaged hair. More particularly, the present invention provides a method and system for repairing the protein structure of damaged hair.

Scientific study has shown that human hair comprises approximately 94% protein and that the hair's protein structure is affected most significantly by pH. The optimum pH of the hair is from about 4.5 to about 5.5. Altering this pH range by applying to the hair water (pH 7), hair treatments or other chemicals having a pH above or below this range results, over time, in damage to the hair's protein structure. In the most severe cases, protein is actually removed from the hair fibers creating holes or spaces in the protein structure of the hair. In general, solutions applied to the hair having a pH higher than about 5.5 tend to relax the normal degree of coil characteristic of normal hair's protein structure, which causes the hair to become limp and bodiless. On the other hand, solutions applied to the hair having a pH lower than about 4.5 tend to tighten the coiled protein structure, and under conditions of extreme acidity such solutions cause the hair to become dry, brittle and almost crystalline in structure.

A number of treatments are known to those skilled in the art for repairing damaged hair. In general, such treatments attempt to repair damaged hair protein through the application of pH-balanced shampoos or protein conditioners. The application of a pH-balanced shampoo will certainly help restore the normal pH of the hair but will do little to repair the hair's damaged protein structure. Conditioners can serve as a source of protein which temporarily attaches to the hair fiber. However, the protein provided by such conditioners is incorporated only slightly into the protein structure of the hair and is easily washed out the next time water or shampoo is applied to the hair. Even in the case of so-called "deep conditioners", the protein is washed out within 2 or 3 days after application.

Accordingly, it is an object of the present invention to provide a method for treating damaged hair by which the normal pH of the hair is restored and the protein structure of the hair is repaired.

It is a further object of the invention to provide a system of compositions for carrying out such a method.

SUMMARY OF THE INVENTION

In one aspect, the present invention meets these and other objects by providing a method for treating damaged hair which includes the steps distributing a first protein conditioner through the hair, distributing an aqueous solution comprising a positively charged electrolyte and an acid through the hair, rinsing the aqueous solution from the hair, and distributing a moisturizer through the hair.

In the preferred embodiment of the process taught by the invention, the hair is cleaned and rinsed prior to distributing the first protein conditioner and then rinsed with water after the first protein conditioner has been distributed. The second step of the process is further characterized in that the aqueous solution contains a second protein conditioner.

In a second aspect, the invention provides a system for treating damaged hair according to the above-described method. The system includes a first protein conditioner, an aqueous solution including a positively charged electrolyte and an acid, and a moisturizer.

The first protein conditioner is applied in the initial step of the process to provide a source of protein for incorporation into the protein structure of the damaged hair. The aqueous solution provides a pH in the range of from about 3 to about 5 and a positive electrolyte which supports the process of incorporating the protein into the hair and the reconstruction of the hair's protein structure, as will be explained more fully below. The moisturizer applied in the final step of the process balances the hair's moisture content. It is important to note here that proper repair of the hair's protein structure in the first and second steps of the process allows the moisture balance of the hair to be maintained for an extended period of time.

DETAILED DESCRIPTION OF THE INVENTION

According to the process taught by the invention, a protein conditioner is applied to the hair after shampooing and rinsing. A number of commercial conditioners well-known to those skilled in the art are suitable for this purpose including vegetable, animal, organic, silicon-based or synthetic protein conditioners. Some of the preferred conditioners include those containing the human hair protein keratin, such as "Avada Deep Penetrating Conditioner" sold by Avada Corp., Minneapolis, Minn., and those containing hydrolyzed vegetable proteins, such as "KMS Ultra-Pak Reconstructor" sold by KMS Research, Inc., Redding, Calif. Another protein conditioner found to be particularly useful contains a mixture of the proteins keratin and collagen as well as amino acids and is sold under the trade designation "Nexxus Keraphix Reconstructor" by Nexxus Products Co., Santa Barbara, Calif.

The protein conditioner is applied to wet hair and is manually distributed throughout the hair for a period of time sufficient to insure an even distribution. Typically, from about one sixteenth ounce to about four ounces, preferably about one-half ounce of protein conditioner is applied to the hair, and a thorough and even distribution typically requires a time period of from about 10 seconds to about 20 minutes, preferably 30 seconds to about 2 minutes. In the preferred embodiment of the invention, once the protein conditioner has been applied and distributed, it is rinsed from the hair with water.

It should be appreciated that the above-cited ranges for quantity and time duration are those typically employed and that the invention is in no way limited in this regard. For example, it has been found that bleached hair and hair that has been subjected to both a permanent treatment and either frosting or coloring generally requires that the protein conditioner remain in the hair for about 2 to about 30 minutes and preferably from about 4 to about 8 minutes.

During this step of the process, the protein contained in the conditioner attaches to the hair fibers and begins to be incorporated into the hair's protein structure. In particular, the protein from the conditioner begins to fill the holes and spaces created by alteration of the hair's normal pH. In general, cleaning the hair and then distributing the conditioner through it is all that is required for initiating the process of incorporating protein into the damaged protein structure. However, it has been found that with respect to the double treated permed hair discussed above, the application of heat facilitates incorporation of the protein from the conditioner. The application of heat in these instances is typically accomplished through the use of a hair dryer, heat lamp or other heating devices typically used by those skilled in the art.

After the protein conditioner has been distributed through the hair, and preferably rinsed out, an aqueous solution including a positively charged electrolyte and an acid is distributed through the hair. This solution is left on the hair for a period of from about 5 seconds to about 2 minutes or more. Preferably, the aqueous solution is left in the hair for a period of from about 45 seconds to about 1 minute. The acid is present in an amount sufficient to provide a pH for the solution of from about 1 to about 8 and preferably from about 3 to about 5. The solution is adjusted to this pH range so that when it is applied to the hair it causes the hair to readopt its normal coiled conformation. As noted above, damaged hair having a pH above that of normal hair has a less coiled conformation than normal hair, and damaged hair having a lower than normal pH has a tightly coiled conformation, which at extremely low pH has an almost crystaline conformation. Almost any mild acid may be used for this purpose, such as asetic acid or citric acid, but citric acid is preferred.

The positively charged electrolyte is included in the aqueous solution to facilitate the incorporation of the protein applied in the initial step of the process into the protein structure of the hair. In the preferred embodiment of the invention, the electrolyte is magnesium, although it should be understood that the invention is in no way limited in this regard.

The electrolyte itself becomes attached to the hair fiber and forms a charged support for the protein. Such a support is required since hair damaged to the extent of losing its natural properties typically exhibits a negative charge which counters the incorporation of protein into the hair. It has been found that the electrolyte not only allows a more complete incorporation of protein into the damaged hair, but also results in the retention of the protein within the hair for far longer periods of time than are possible with prior art attempts to treat damaged hair by applying a protein conditioner.

As noted above, in the preferred embodiment of the invention the aqueous solution provides an additional source of protein for incorporation into the damaged hair. Any water soluble vegetable, animal, organic or synthetic liquid protein conditioner known to those skilled in the art may be used for this purpose. In the preferred embodiment of the invention, a liquid vegetable protein conditioner available under the trade designation KMS Process Protector"from KMS Research, Inc., Redding, Calif. is used.

In typical applications, the aqueous solution is compounded with from about 0.1 gm to about 30 gm of citric acid and preferably about 1 to 6 gms, form about 2 gm to more than 8 gm of magnesium carbonate (7.5 cc to about 30 cc of a 27.3% solution of magnesium carbonate) and with from about 7.5 cc to about 30 cc of liquid protein conditioner. Of course, solutions of different magnesium salts, such as magnesium sulfate, and of varying strength may be used as long as a corresponding weight of magnesium ion is provided. In the preferred embodiment, a 27.3% solution of magnesium carbonate available from Marianna Corp., Omaha, Nebr., is employed. Additional water may be added to the solution if desired, and typically from about 1 ounce to about 7 ounces of water is added. Example 1 sets forth a preferred formulation for the aqueous solution applied in the second step of the process.

EXAMPLE 1

| Citric Acid | 2.8 gm |
|---|---|
| Magnesium Carbonate | 30 cc (27.3% w/v) |
| Water soluble protein | 30 cc |
| Water | q.s. 240 cc |

In the final step of the process, a moisturizer is distributed through the hair to restore its normal moisture balance. Typically, from about one-sixteenth to about 2 ounces, preferably about one-half to about one and a half ounces, of the moisturizer is applied, although more or less may be used depending on each particular case. It has been found that the hair effectively absorbs moisture only when the damaged protein structure of the hair has been properly repaired and the natural conformation of the hair protein has been restored according to the first two steps of the process. Almost any moisturizer commonly used by those skilled in the art may be employed; however, "Nexxus Humectress Moisturizer", available from Nexxus Products Co., Santa Barbara, Calif. and "Replace Moisturizer" available from KMS Research, Inc., Redding, Calif. are preferred.

The process of treating damaged hair taught by the invention and the system of formulations for carrying out the process result in a complete restoration of the hair's normal characteristics regardless of hair type. Testing was performed on hundreds of individuals presenting all varieties of hair, including short, medium length and long hair, thick, medium diameter and fine hair, naturally curly, wavy and straight hair, and thinning or sparse hair. In all cases following treatment the previously damaged hair was soft to the touch, had no tangles or dry ends and, especially in the case of individuals with fine or sparse hair, showed a clear increase in thickness.

Hair treated by the above described method and system of formulations also shows added body and manageability when styled and will hold styling for longer periods of time. Following chemical treatment, such as bleaching, perming, straightening, coloring or frosting, treatment of the hair according to the invention provides the hair with a soft look and touch, and noticeably more shine. Tangles and dry ends are virtually eliminated. These same results are consistently achieved in the case of double processed hair, i.e., frosted or colored hair that is also permed. In should be noted however, that in some of these cases, particularly with hair that is bleached or frosted and permed together, it has been shown to be advantageous to reduce the amount of citric acid by about half and to subject the hair to heat for up to five minutes during the first step of the process.

It has been found that the positive results of the treatment process typically last for about two to six weeks. Generally, after about two to three weeks of daily washing and styling, the hair begins to loose its shine and body, and tangles and dry ends begin to appear. If treatment is not repeated by about the six week period, the hair will again begin to show serious structural damage. Intervals between treatment can be prolonged if the individual uses high quality shampoos and conditioners.

While preferred embodiments have been shown and described, various modifications and substitutions may be made without departing from the spirit and scope of the invention. Accordingly, it is to be understood that the present invention has been described by way of example and not by limitation.

I claim:

1. A method for repairing damaged hair, said method comprising the steps of:
   (a) distributing a first source of protein through the damaged hair;
   (b) applying an aqueous solution to the damaged hair, said solution including a positively charged electrolyte, said electrolyte providing a charged support for the protein provided in step (a) to incorporate the protein into the damaged hair, and sufficient acid to provide the solution with a pH of from about 1 to about 8;
   (c) rinsing the aqueous solution form the damaged hair; and
   (d) distributing a moisture balance for the damaged hair.

2. The process of claim 1 wherein the aqueous solution includes sufficient acid to have a pH of from about 3 to about 5.

3. The process of claim 1 wherein the acid is citric acid.

4. The process of claim 1 wherein the positively charged electrolyte is magnesium.

5. The process of claim 1 wherein the aqueous solution further comprises a second protein conditioner.

6. The process of claim 1 wherein after step (a) and before step (b) the process includes the step of rinsing the hair with water.

7. A process for treating damaged hair comprising the steps of:
   (a) cleaning the hair by shampooing and rinsing;
   (b) distributing a first protein conditioner through the hair to provide a first source of protein;
   (c) rinsing the first protein conditioner from the hair with water;
   (d) distributing an aqueous solution through the hair, said solution including a second protein conditioner to provide a second source of protein, sufficient acid to provide the solution with a pH of from about 3 to about 5, and magnesium, said magnesium providing a positively charged support for the protein provided by the first and second conditioners to incorporate the protein into the damaged hair.

* * * * *